(12) United States Patent
Lang et al.

(10) Patent No.: US 6,500,189 B1
(45) Date of Patent: Dec. 31, 2002

(54) MEDICAL INSTRUMENT FOR DISSECTING TISSUE

(75) Inventors: Dieter Lang, Stockheim (DE); Uwe Bacher, Tuttlingen (DE); Fridolin Anders, Immendingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/563,755

(22) Filed: May 1, 2000

(30) Foreign Application Priority Data

Apr. 29, 1999 (EP) .............................. 99108380

(51) Int. Cl.⁷ .............................................. A61B 17/32
(52) U.S. Cl. ...................................... 606/170; 606/205
(58) Field of Search ............................... 606/159, 170, 606/174, 205–210, 564, 566, 567; 600/565

(56) References Cited

U.S. PATENT DOCUMENTS

| | | | | | |
|---|---|---|---|---|---|
| 3,837,345 A | * | 9/1974 | Matar | ........................ | 606/171 |
| 4,243,048 A | * | 1/1981 | Griffin | ........................ | 600/567 |
| 4,646,745 A | | 3/1987 | Noiles | | |
| 4,945,920 A | * | 8/1990 | Clossick | ..................... | 606/205 |
| 5,152,744 A | * | 10/1992 | Krause et al. | .............. | 606/170 |
| 5,476,473 A | | 12/1995 | Heckele | | |
| 5,507,772 A | | 4/1996 | Shutt et al. | | |
| 5,620,415 A | * | 4/1997 | Lucey et al. | ................ | 600/565 |
| 5,851,212 A | * | 12/1998 | Zirps et al. | ................. | 606/174 |

FOREIGN PATENT DOCUMENTS

| | | |
|---|---|---|
| DE | 87 12 835.7 | 1/1988 |
| DE | 4300064 A1 | 7/1994 |
| DE | 19520717 A1 | 12/1996 |

* cited by examiner

Primary Examiner—Bruce Snow
(74) Attorney, Agent, or Firm—St. Onge Steward Johnston & Reens LLC

(57) ABSTRACT

A medical instrument for dissecting tissue in the human or animal body comprises a shaft. At least one movable tool is arranged at a distal end of the shaft. At least one movable grip element is arranged at a proximal end of the shaft. A force transmission element extends along the shaft, which force transmission element is movable relative to the latter and transmits thrust and/or tension forces and whose proximal end is non-positively joined to the at least one movable grip element and whose distal end is non-positively joined to the at least one movable tool. The shaft is further provided with a bend at at least one point between the distal end and the proximal end. The force transmission element is configured, at least in the region of the bend, as a flexible tubular element conforming to the bend, which is guided in contact with the shaft. According to a second variant, a flattened and flexible configuration is given to the force transmission element in the region of the bend, at least locally transversely to the plane of curvature of the bend, and the force transmission element extends continuously in axial direction, transversely to the plane of curvature, at least over the inner diameter of the shaft in the region of the bend.

9 Claims, 7 Drawing Sheets

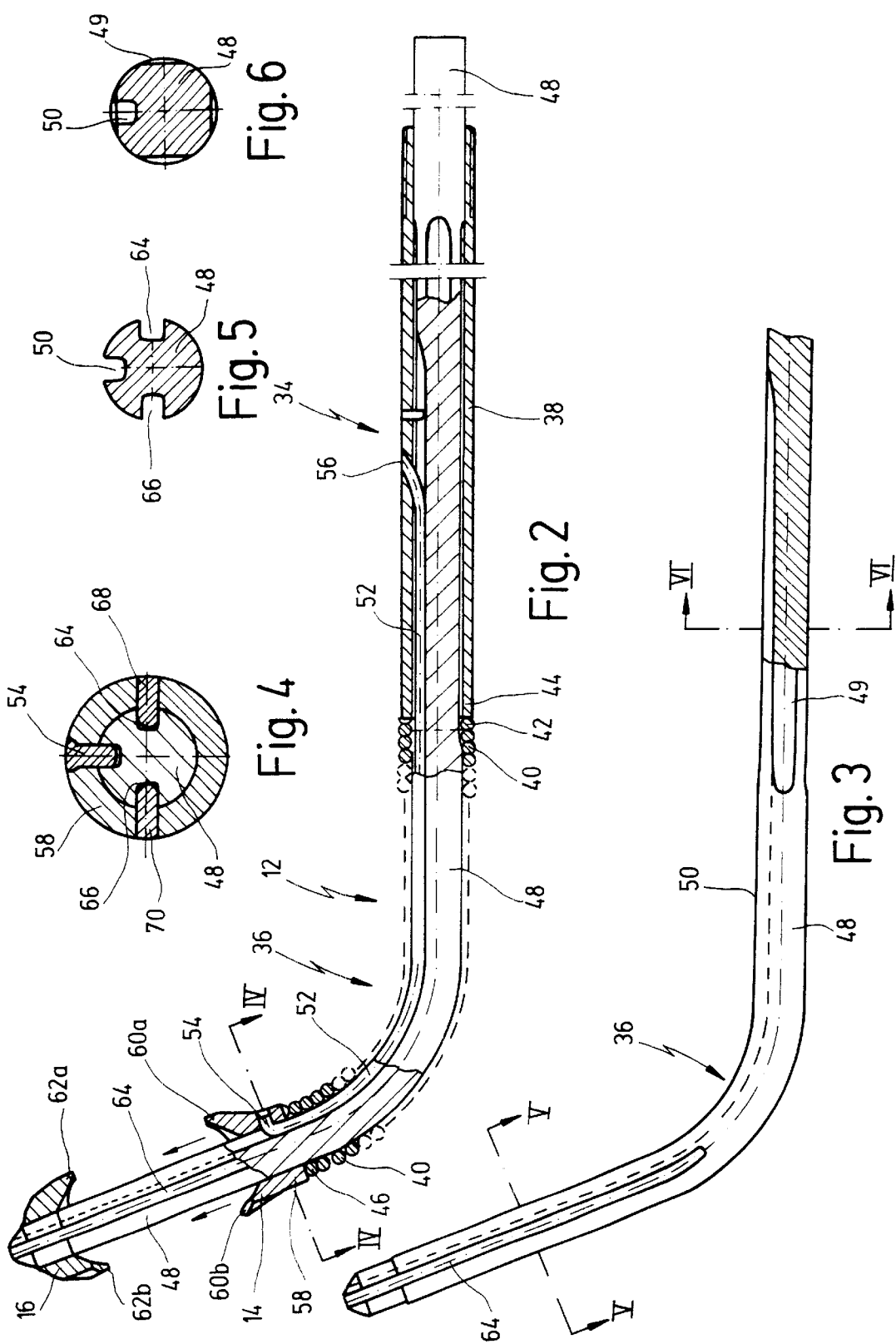

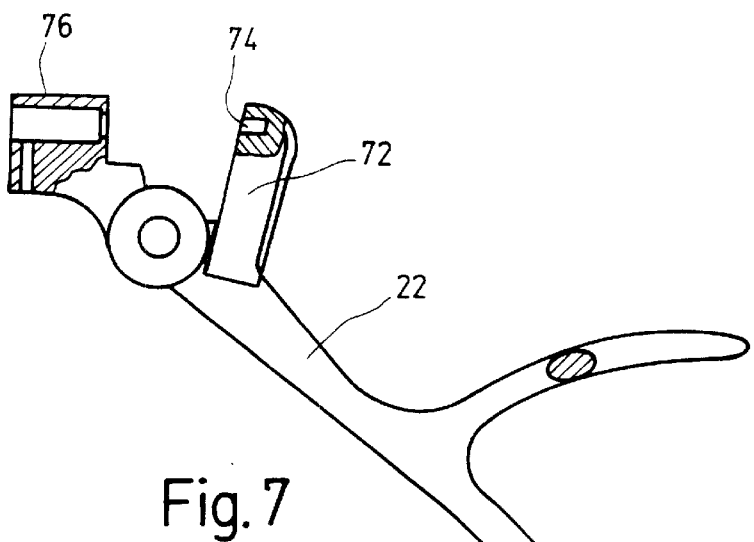
Fig. 7
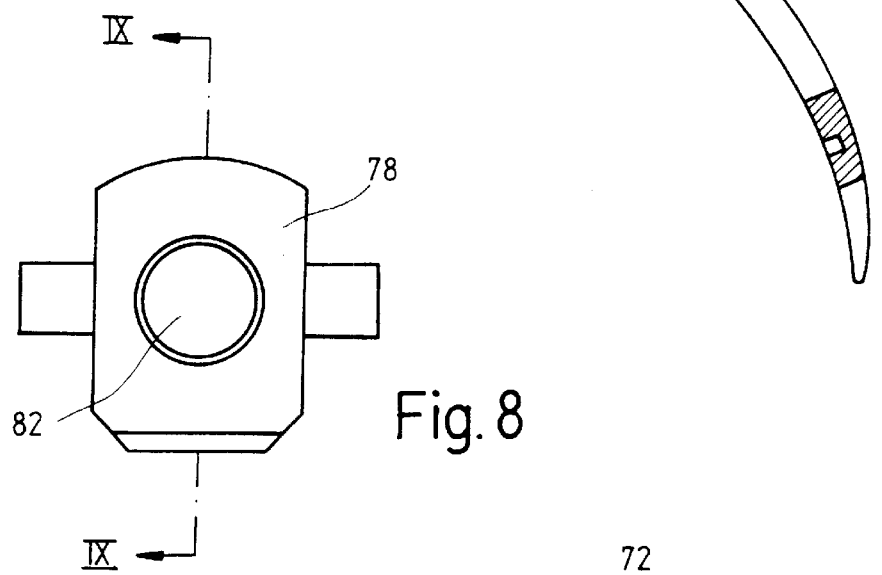
Fig. 8
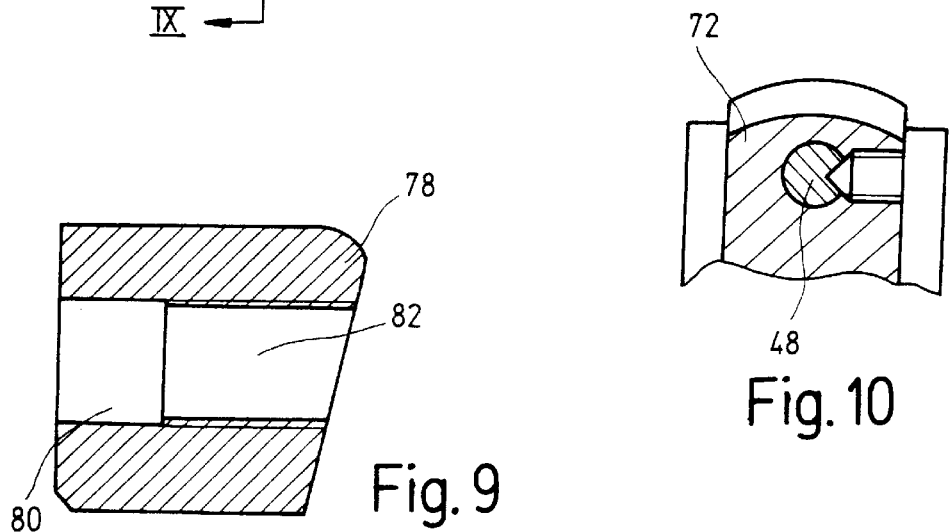
Fig. 9
Fig. 10

MEDICAL INSTRUMENT FOR DISSECTING TISSUE

BACKGROUND OF THE INVENTION

The present invention relates to a medical instrument for dissecting tissue in the human or animal body.

An instrument for dissecting tissue is one used for cutting and for grasping tissue, for example a punch, a pair of scissors or a forceps.

Instruments of this kind are used in the context of minimally invasive surgery for dissecting tissue in the human or animal body, usually under endoscopic monitoring. To this end, instruments of that kind comprise an elongated shaft which has at least one movable tool arranged at its distal end, which usually coacts with another movable or immovable tool, arranged at the distal end of the shaft, for dissecting the tissue. For operating the at least one movable tool, such instruments are further provided, on the proximal end of the shaft, with at least one movable grip element through which the axially movable force transmission element, transmitting thrust and/or pull forces, is non-positively connected with the at least one movable tool so that any movement of the movable grip element is translated by the force transmission element into a movement of the movable tool.

Especially for operations in the region of the ear, nose and throat one normally uses instruments with a shaft having at least one bend in order to permit the tool or tools arranged on the distal end to be advanced to positions that are accessible only with difficulty, for example into niches in the frontal or the maxillary sinus.

An instrument with a bent shaft, especially if the bending radius is small, presents the problem that the force must be transmitted by the force transmission element from the movable grip element through the bend to the movable tool. This is rendered difficult especially in view of the aim to have a slim instrument, i.e. one with a thin shaft.

In order to be able to adapt itself to the bend, the force transmission element must, therefore, be flexible in the region of the bend of the shaft.

DE 44 44 025 A1 discloses, for example, a force transmission element for a medical instrument in the form of a flexible wire element, which is capable of adapting itself to such a bend. However, a flexible wire can transmit only tensile or pull forces, but is not suited for transmitting thrust, or even high thrust. For, if the force transmission element is subjected to thrust, the wire will buckle so that only small, or no thrust can be transmitted to the at least one movable tool for actuating the latter for the purpose of dissecting tissue.

Considering, however, that such instruments are also used for cutting hard tissue, for example cartilage or bone tissue, the nature of the force transmission element must be such to permit even very high forces, especially high thrust forces, to be transmitted to the movable tool without any buckling of the force transmission element, and this, of course, although the transfer of forces must be effected through the bend of the shaft, which means that the force transmission element must be capable of adapting itself to the bending radius during its axial movement.

DE 195 20 717 C2 proposes to solve this problem with the aid of a tubular-shaft instrument with a tubular shaft provided with a bend, where the force transmission element is arranged inside the tubular shaft. In the bent portion of the tubular shaft, the force transmission element is configured as a bar made from a flexible material, which is in contact with the inner wall of a surrounding rigid sleeve, extending concentrically to the shaft, and whose cross-section is reduced, in the region of the bend, by a number of circumferential grooves arranged one beside the other in axial direction. The before-mentioned sleeve may be constituted also by the tubular shaft as such. The circumferential grooves are formed to extend over the full circumference of the bar. Thus, the bar is locally reduced in thickness to sort of a wire with circular cross-section in the region of the circumferential grooves. In the intermediate sections between the grooves, the diameter of the bar is not reduced so that the outer surfaces of the intermediate sections serve as guide surfaces to guide the force transmission element in the region of the bend in contact with the inner wall of the sleeve and/or the tubular shaft.

Although such a force transmission element permits high thrust forces to be transferred through the bend to the movable tool, this known instrument nevertheless must be regarded as disadvantageous with that configuration of the force transmission element.

Considering that such instruments are used in minimally invasive surgery, it is another demand that must be placed on such instruments that their diameter in the region of the shaft be as small as possible to permit the instrument, together with the shaft, to be introduced into an incision or natural opening in the body which should be as small as possible. In the case of such miniaturized instruments with a shaft diameter of a few millimeters only, this means for the known instrument that the force transmission element has an extremely small diameter in the reduced regions of the circumferential grooves, whereby the stability of the force transmission element is reduced because the material thickness of the force transmission element is reduced to very small wire cross-sections in the region of the circumferential grooves. Therefore, the force transmission element may buckle or break in the region of the circumferential grooves extending over the full circumference when high thrust or sudden thrust is transferred, or may fracture when high pull forces are transferred, whereby the operating safety of the known instrument is reduced.

DE 43 00 064 A1 discloses a punch for dissecting tissue having an outer shaft and an inner shaft, at a distal end of which an opening having a blade is provided, which coacts with a counter blade at the distal end of the outer shaft in such a way that, upon actuation of the punch, tissue which protrudes through said opening in the inner shaft, is cut off by the blades moved against each other. The inner shaft is formed rigid, is straight in the proximal region and merges distally into a curved course, and the outer shaft, which forms the force transmission element of this instrument, is at least in the region of this curvature deformable. The deformability of the outer shaft is made possible by that the outer shaft is provided with recesses which face each other on the radius of the curvature of the inner shaft. The recesses in form of radial incisions or notches only leave a narrow bridge of material between themselves.

U.S. Pat. No. 5,507,772 also discloses a medical instrument, the shaft of which comprises a bend. The force transmission element comprises a plurality of notched or recessed sections in the region of the bend of the shaft. Between the recessed sections of the force transmission element a plurality of ribs are formed, the thickness of which substantially conforms to the thickness of the remaining body of the force transmission element. The ribs are formed in direction of one side of the force transmission element only, whereas the force transmission element is configured continuously flat in the region of the bend on the opposite side of the ribs. The force transmission element and the ribs thereof are guided in an elongated slot inside the shaft, which slot is provided in the concave inner side of the bend of the shaft. In another embodiment, the ribs are omitted so that, in this case, the force transmission element is configured in the region of the bend as a flat band, which, however, is not guided in this case.

U.S. Pat. No. 4,646,745 further discloses a medical stapler, which comprises a force transmission element disposed within said shaft, wherein the force transmission element is configured in form of a flat band, so that the force transmission element is flexible. The flat band itself consists of three sheets of thin bands. In the region of a bend of the shaft, the flat band is guided along a spacer element, in order to achieve that the flat band maintains its central position in the shaft in the region of the bend, if the flat band is under tension, i.e. in order to prevent the flat band from becoming straight in the region of the bend of the shaft. The spacer element is provided with ball bearings for reducing the friction between the force transmission element and the space element.

Now, it is the object of the present invention to improve a medical instrument of the before-mentioned kind in such a way that high pull and/or thrust forces can be transferred to the at least one movable tool by means of the force transmission element, through the bend of the shaft, without any buckling of the force transmission element and without any reduction in stability of the force transmission element being encountered in the region of the bend.

SUMMARY OF THE INVENTION

In a first aspect of the invention, this object is achieved according to the invention by a medical instrument for dissecting tissue in the human or animal body, comprising:
- a shaft having a distal end and a proximal end, said shaft having at least one bend between said distal and said proximal end;
- at least one movable tool disposed at said distal end of said shaft;
- at least one movable grip element disposed at said proximal end of said shaft;
- a force transmission element having a distal end a proximal end and extending along said shaft and, further, being movable relative to said shaft, said proximal end of said force transmission element being operatively interconnected to said at least one movable grip element and said distal end of said force transmission element being operatively interconnected to said at least one movable tool for transmitting a force from said at least one movable grip to said at least one movable tool,
- wherein said force transmission element is configured, at least in the region of said bend, as a flexible tubular element conforming to the bend, which is guided in contact with said shaft, and wherein said tubular element is configured as a helical spring with closely wound windings.

Consequently, it is provided according to the first aspect of the instrument according to the invention that the force transmission element is configured, at least in the region of the bend, as a flexible tubular element in form of a helical spring, which is guided in contact with the shaft. It is an advantage of such a flexible tubular element that it can be made from material of substantially the same thickness throughout. By having the flexible tubular element guided in contact with the shaft, in the region of the bend, the tubular element is prevented from buckling because any lateral deflection of the tubular element during transfer of thrust forces is rendered impossible by the guiding relationship between the element and the shaft. The configuration of the force transmission element of the instrument according to the invention is suited both for cases where the force transmission element is arranged inside a shaft configured as a tubular shaft, and for cases where the force transmission element as such is configured as tubular shaft and guided on the outside of the shaft. Due to the fact that the tubular element can be given the same material thickness over its full axial length, thinner regions as encountered in the known instrument, where the force transmission element is reduced to the shape of a wire in the regions of the circumferential grooves, are avoided whereby higher overall stability and, thus, improved operating safety of the force transmission element and, thus, of the whole instrument is achieved.

The configuration of the flexible tubular element as a helical spring is of particular advantage because a helical spring, consisting of steel, for example, is rigid in radial direction but presents high elasticity along its longitudinal axis because the windings of the helical spring a capable of moving one relative to the other when the helical spring is bent. By giving the helical spring closely wound windings, high thrust forces can be transferred by the helical spring to the movable tool, without any loss of force and without delay, because the helical spring cannot be compressed in axial direction.

According to a further preferred embodiment, the force transmission element is configured as a tube comprising the tubular element in the region of the bend, the tube being arranged around the shaft.

This feature, namely the external arrangement of the force transmission element relative to the shaft, provides the particular advantage, especially in the case of miniaturized instruments with small shaft diameter, that the shaft as such can be given a relatively narrow overall shape, whereas a larger diameter is available for the force transmission element. It is thereby possible to provide an especially strong force transmission element, suitable for transferring high thrust and pull forces, even with instruments of particularly narrow overall shape.

According to a further improved embodiment, the shaft comprises a solid bar made from solid material.

It is an advantage of this feature that due to the configuration of the shaft as a solid bar a particularly strong instrument body is obtained that gives the instrument particularly high stability against bending stresses exerted on the shaft.

It is further preferred if the tubular element is connected with the remaining tube by a substance bond.

This feature is of advantage in terms of easy manufacturability of the force transmission element since the tubular element, especially if in the form of a helical spring, and the remaining tube of the force transmission element can be manufactured by separate processes and can be connected thereafter by soldering, welding or bonding. Another advantage of that feature lies in the fact that the helical spring and the remaining tube constitute a single component, which facilitates the assembly and disassembly procedures of an instrument that can be taken apart to its shaft and force transmission element.

According to a further preferred embodiment, the tubular element is directly connected with the movable tool.

It is an advantage in this connection that in cases where the bend is arranged close to the distal end of the shaft an instrument can be realized that has a short axial length on the distal side of the bend.

According to a further preferred embodiment, the movable tool is connected with the remaining tube in non-positive fashion, by means of a flexible pull element parallel to the tubular element.

It is an advantage in this connection that even high tensile or pull forces can be transferred over the bend, the tensile forces being then absorbed by the flexible pull element, whereby it is additionally avoided that the tubular element, if in the form of a helical spring, will expand axially under tensile stress exerted on the force transmission element, so that it is always guaranteed, also when tension is transferred, that the movable tool is properly entrained. The pull element may in this case take the form of a band, a wire or a strand made from metal, carbon fiber or Kevlar.

It is further preferred in this connection if the shaft comprises a groove, in the region of the bend, in which the pull element is guided between the tubular element and the shaft.

This arrangement provides the advantage that the pull element, too, is guided and retained with little play over the bend, between the helical spring and the shaft, during axial movements of the force transmission element.

According to a further preferred embodiment, the pull element is directly connected with the at least one movable tool.

This feature advantageously guarantees that the at least one movable tool is moved any time a tensile force is exerted upon the flexible pull element.

According to a further preferred embodiment of the instrument according to the invention, the shaft and the force transmission element are detachable from each other.

It is an advantage of this arrangement that contaminants that may collect in the region of the tubular element and also in the remaining region of the shaft, between the force transmission element and the shaft, can be removed easily and safely whereby the cleaning properties of the instrument according to the invention are improved.

In a second aspect of the invention the object underlying the invention is achieved by a medical instrument for dissecting tissue in the human or animal body, comprising:

a shaft having a distal end and a proximal end, said shaft having at least one bend between said distal and said proximal end;

at least one movable tool disposed at said distal end of said shaft;

at least one movable grip element disposed at said proximal end of said shaft;

a force transmission element having a distal end and a proximal end and extending along said shaft and, further, being movable relative to said shaft, said proximal end of said force transmission element being operatively interconnected to said at least one movable grip element and said distal end of said force transmission element being operatively interconnected to said at least one movable tool for transmitting a force from said at least one movable grip to said at least one movable tool;

said force transmission element being configured, at least in the region of said bend and at least sectionally transversely to a plane of curvature of said bend, flattened and flexible, and said force transmission element extending in the region of said bend in the direction transversely to said plane of curvature of said bend continuously in axial direction at least over an inner diameter of said shaft, and said force transmission element comprising a plurality of axially spaced flattened sections, wherein said force transmission element is in contact by its circumference with said shaft in intermediate sections between said flattened sections, and wherein said intermediate sections extend to both a concave and a convex inner side of said bend of said shaft.

With an instrument comprising a shaft in the form of a tubular shaft and a force transmission element arranged inside the tubular shaft, it is provided to give the force transmission element a locally flattened flexible configuration in axial direction, at least in the region of the bend. Flattened means in this connection that in the flattened region the force transmission element is not reduced in thickness to wire cross-section over its full circumference, as in the prior art, but is reduced in such a way that the force transmission element still extends over the entire inner diameter of the shaft in the flattened regions.

Accordingly, the force transmission element comprises webs or band-like sections in the flattened regions. The flattened regions may also consist of incisions in the force transmission element, that extend transversely to the lengthwise axis and also transversely to the plane of curvature, the force transmission element otherwise being preferably made of solid material. The configuration of the force transmission element with flattened sections in the region of the bend gives the force transmission element flexibility in the plane of curvature, which is absolutely sufficient since the bend of the shaft only requires flexibility of the force transmission element in the plane of curvature. The configuration of the force transmission element with flattened sections in the region of the bend and the extension of those sections over the inner diameter of the shaft provides, however, the advantage that the force transmission element offers high stability in spite of the reduced material thickness in the region of the flattened sections since it is exactly those sections that extend over the full width of the shaft. Consequently, contrary to the instrument known from the before-mentioned DE 195 20 717 C2, where the force transmission element is reduced to wire cross-section over the full circumference in the region of the bend of the shaft, a force transmission element, which is strong in the region of the bend, is thereby provided even in cases of miniaturized configuration of the instrument with a very small shaft diameter.

The intermediate sections between the flattened sections ensure that the force transmission element is guided with small play in the shaft, in the region of the bend, and prevent any buckling of the force transmission element in the region of the bend in the plane of curvature.

It is further preferred in this context if the flattened sections of the force transmission element are formed from solid material by a machining process where the flattened sections may be formed, for example by a milling operation, by removing material from two circumferential opposite sides of the force transmission element in a direction transversely to the lengthwise direction of the force transmission element. This also simplifies the manufacture of the force transmission element, compared with the force transmission element of the known instrument, since in the latter case the circumferential grooves must be formed by a turning operation on a lathe.

According to another preferred embodiment, each of the flattened sections is formed at the same axial position from two opposite sides of the circumference of the force transmission element.

This feature provides the advantage that central areas in the form of flat bands can be formed relative to the lengthwise axis of the force transmission element, for which the maximum diameter of the force transmission element is available.

According to an alternative preferred embodiment, the flattened sections are formed in axially offset arrangement from opposite sides of the circumference of the force transmission element.

In the case of this embodiment, the flattened portions are provided in alternating arrangement at offset circumferential positions, similar to a meander, which provides the advantage that while being likewise flexible in cross-section in the unilaterally flattened sections, the force transmission element nevertheless offers high stability.

In a third aspect of the invention, the object underlying the invention is achieved by a medical instrument for dissecting tissue in the human or animal body, comprising:

- a shaft having a distal end and a proximal end, said shaft having at least one bend between said distal and said proximal end;
- at least one movable tool disposed at said distal end of said shaft;
- at least one movable grip element disposed at said proximal end of said shaft;
- a force transmission element having a distal end a proximal end and extending along said shaft and, further, being movable relative to said shaft, said proximal end of said force transmission element being operatively interconnected to said at least one movable grip element and said distal end of said force transmission element being operatively interconnected to said at least one movable tool for transmitting a force from said at least one movable grip to said at least one movable tool;
- said force transmission element being configured, at least in the region of said bend and continuously in axial direction, as an axially flat band extending in the region of said bend in direction transversely to a plane of curvature of said bend, wherein narrow sides of said bend are guided in lateral guides in said shaft.

This medical instrument according to a third aspect of the present invention provides the advantage that the flexible configuration of the force transmission element in the region of the bend of the shaft is particularly simple, both in terms of design and manufacturing technique. By having the narrow sides guided in lateral guides in the shaft any buckling of the force transmission element in the region of the bend is prevented in this case as well.

It is preferred in this connection if the guides are formed as grooves in an inner wall of the shaft.

This feature provides the advantage that the shaft can be closed in the region of the bend whereby any penetration of contaminants into the shaft can be avoided.

Alternatively, it is however also preferred if the guides are configured as open slots in the shaft.

This feature provides the advantage that the slots can be introduced into the shaft in an especially simple way, in terms of manufacturing technique, so that the manufacturing expense of the instrument is reduced in the case of this embodiment.

According to a further preferred embodiment of all the aforementioned instruments, the force transmission element is configured as a solid bar, consisting of solid material, in regions outside the bend.

It is an advantage of this arrangement that the force transmission element can be made especially strong and rigid in regions outside the at least one bend, especially over elongated straight regions of the shaft, which makes the force transmission element particularly well suited for the transfer of high thrust.

According to another preferred embodiment, the flat band of the instrument according to the third aspect of the invention is formed from the bar by a machining operation.

This feature provides the advantage that the flat band and the remaining body of the force transmission element are made as a single piece, whereby any predetermined breaking points, for example in the form of soldering, welding or bonding points, can be avoided.

Alternatively, it is however also preferred if the band is connected with the bar by a substance bond.

This is of advantage in cases where it is meaningful for reasons of manufacturing technique to produce the bar and the band by separate processes.

According to another preferred embodiment of the instruments according to all of the three aspects, the at least one movable tool is axially movable relative to the shaft, and a second tool is arranged at the distal end of the shaft, the movable tool and the second tool acting together in the way of a punch if moved axially one relative to the other.

Such an embodiment offers the advantage, especially if used in very restricted operating regions, for example in the frontal or maxillary sinus, that the two tools do not need a free operating radius beyond the circumference of the shaft, for dissecting tissue, because both tools are moved relative one to the other only in the axial direction of the shaft, or more precisely, in the lengthwise direction of the distal end of the shaft.

It is further preferred in this connection if the second tool is connected with the shaft immovably, and is arranged distally before the movable tool.

This arrangement provides the advantage that the second immovable tool forms the distal point of the shaft and defines a stationary working point when that immovable tool is applied to the tissue to be dissected. In this case, thrust is exerted by the force transmission element to displace the movable tool in distal direction relative to the immovable tool, in order to cut off the tissue gripped between the immovable tool and the movable tool, and a pull force is exerted for the purpose of separating the two tools again one from the other.

According to another preferred embodiment, the at least one movable tool is protected from torsion relative to the second tool.

This feature is of advantage especially in connection with that medical instrument which has the force transmission element configured as a tube and as a helical spring in the region of the bend. The protection from torsion retains the movable tool and the second tool in fixed positions one relative to the other, with respect to torsion about the longitudinal axis of the shaft, and this even under rotary forces acting on the helical spring.

As an alternative to the configuration of the at least one movable tool as punching tool, the invention can be used, however, with like advantage if the at least one movable tool is configured as a jaw part which can be pivoted about a hinge joint and which coacts with a second tool in the manner of a pair of scissors or a forceps.

Further advantages are evident from the description below and the appended drawings.

It is understood that the features recited above and those yet to be explained below can be used not only in the respective combination indicated, but also in other combinations or in isolation, without leaving the scope of the present invention.

BRIEF DESCRIPTION OF THE DRAWINGS

Exemplary embodiments of the invention are shown in the drawings and will be explained in more detail in the description below. In the drawings:

FIG. 2 shows a partly sectioned side view, in enlarged scale, of the arrangement comprising the shaft and the force transmission element of the instrument according to FIG. 1;

FIG. 3 shows a view, likewise in enlarged scale, of the distal end of the shaft in isolation;

FIG. 4 shows a section taken along line IV—IV in FIG. 2;

FIG. 5 shows a section taken along line V—V in FIG. 3;

FIG. 6 shows a section taken along line VI—VI in FIG. 3;

FIG. 7 shows a side view, partly sectioned, of an isolated immovable grip element of the instrument according to FIG. 1;

FIG. 8 shows a rear view of part of the isolated movable grip element, through which the proximal end of the force transmission element is connected with the movable grip element;

FIG. 9 shows a section taken along line IX—IX in FIG. 8;

FIG. 10 shows a section taken along line X—X in FIG. 1;

DETAILED DESCRIPTION OF PREFERRED EMBODIMENTS

Figure 1:
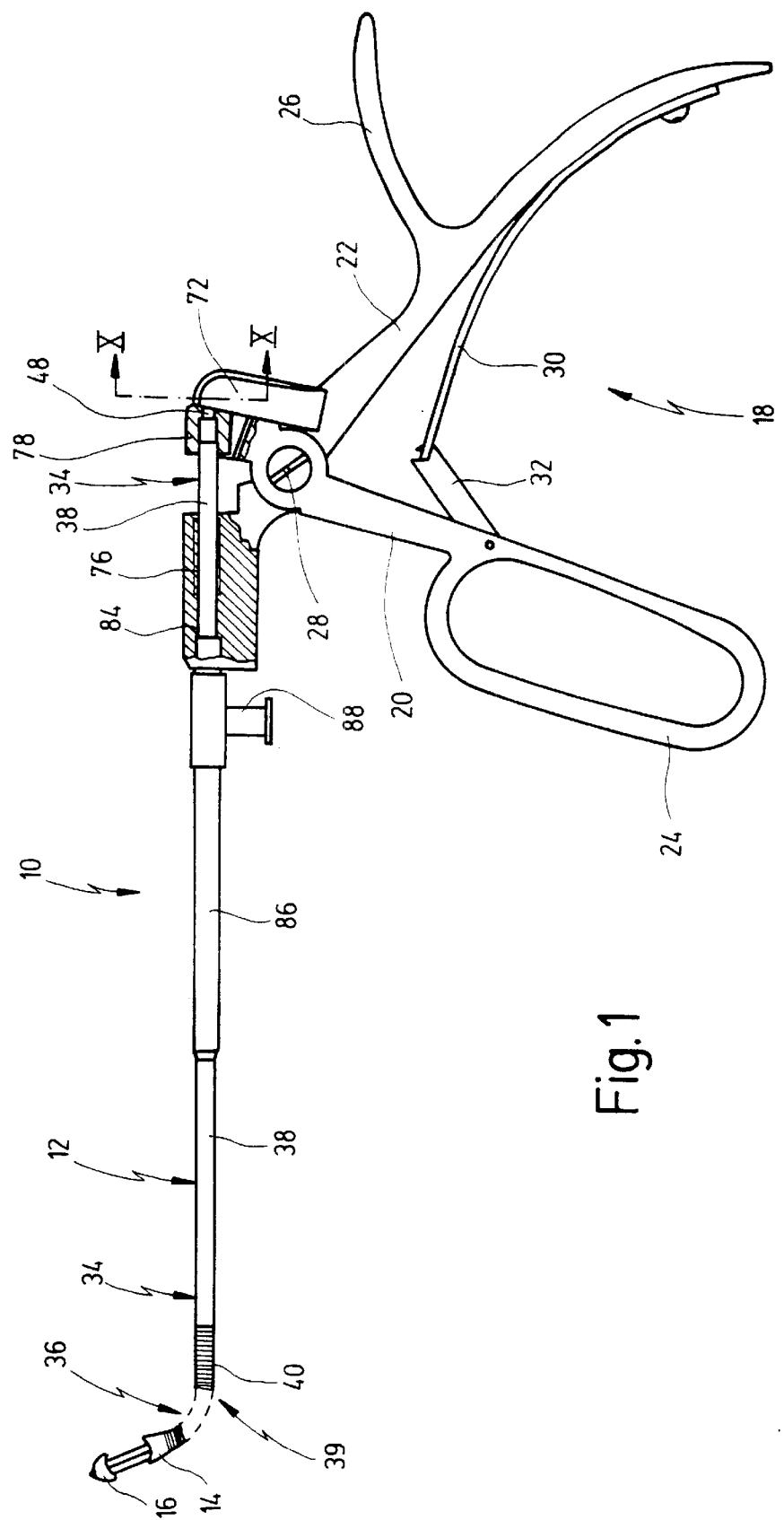
FIG. 1 shows an overall side view, partly sectioned, of one embodiment of the first aspect of the medical instrument according to the invention.

FIG. 1 shows a medical instrument according to a first aspect of the invention, indicated generally by reference numeral 10.

Instrument 10 serves for dissecting tissue in the human or animal body.

Instrument 10 comprises an elongated shaft 12. A movable tool 14 is arranged at a distal end of shaft 12. Further, an immovable tool 16 is arranged at the distal end of shaft 12, distally before movable tool 14.

At the proximal end of shaft 12, a handle 18 is arranged that comprises a movable grip element 20 and an immovable grip element 22.

Movable grip element 20 comprises a ring 24 through which one, two or three fingers can be slipped. Immovable grip element 22 comprises an extension 26, projecting in proximal direction, against which the hollow between the thumb and the index finger comes to rest during operation of the instrument.

Movable grip element 20 and immovable grip element 22 are connected one with the other via a hinge joint 28, a pivot axis of hinge joint 28 extending perpendicularly to the lengthwise direction of shaft 12.

Further, a leaf spring 30 is fixed to immovable grip element 22, which leaf spring 30 is connected with a lever 32 mounted to pivot on movable grip element 20. Leaf spring 30 and lever 32 bias movable grip element 20 to its open position illustrated in FIG. 1, spaced from immovable grip element 22, in which tools 14 and 16 are likewise spaced one from the other.

Movable grip element 20 is connected, in non-positive fashion, with movable tool 14 via an axially movable force transmission element 34, which will be described hereafter in more detail.

Further, shaft 12 comprises a bend 36 located in the region of the distal end of shaft 12. A plane of curvature of bend 36 lies in the plane of drawing in FIG. 1.

According to FIGS. 1 and 2, force transmission element 34 is configured as a tube 38. In the region of bend 36, force transmission element 34 is configured as a flexible tubular element 39 in the form of a helical spring 40, conforming to the bend and extending over bend 36. The helical spring 40 comprises a plurality of closely wound windings consisting of spring steel; in FIGS. 1 and 2 only the region of the distal and the region of the proximal ends of helical spring 40 are shown. It is, however, understood that helical spring 40 extends with its closely wound windings over the entire region of bend 36.

A proximal end 42 of helical spring 40 is connected with a distal end 44 of tube 38 by a substance bond, for example by laser welding. A distal end 46 of helical spring 40 is connected by a substance bond, for example likewise by laser welding, with the proximal end of movable tool 14, whereby a non-positive connection is obtained between force transmission element 34 and movable tool 14.

Shaft 12 comprises a bar 48. Bar 48 is strong and rigid and made from solid material. Tube 38 and, thus, helical spring 40 connected with it are arranged around bar 48 and are guided by their circumference along bar 48 during axial movement. The inner diameter of helical spring 40 and of tube 38 corresponds to the outer diameter of bar 48.

As appears from FIGS. 5 and 6, bar 48 exhibits a circular cross-section, and shaft 12 comprises four circumferentially limited flat sides 49 in the region proximally behind bend 36 so that spaces remain in the region of flat sides 49 between tube 38 and bar 48, which spaces may be used as rinsing cross-sections in order to introduce a rinsing liquid into the operating region, through the space between tube 38 and bar 48.

On its side facing the inner radius of bend 36, bar 48 is provided with a groove 50 in the region of bend 36, in which a flexible pull element 52 is received. Flexible pull element 52 is configured as a flexible wire. Distal end 54 of pull element 52 is connected with movable tool 14 by a substance bond, for example by welding. Starting from movable tool 14, flexible pull element 52 lies in groove 50 of bar 48 within helical spring 40 and has its proximal end 56 connected with tube 38 in a bore provided in the latter, likewise by a substance bond. Flexible element 52 prevents any extension of the helical spring 40 during withdrawal of tube 38, i.e. when force transmission element 34 exerts tensile or pull forces.

Movable tool 14 is arranged on bar 48 for axial movement and comprises for this purpose, at its proximal end, a sleeve section 58 surrounding the circumference of bar 48. Sleeve section 58 as a whole only has a small axial extension.

At the extreme distal end of bar 48, immovable tool 16 is fixed to bar 48, the fixed connection between immovable tool 16 and bar 48 being likewise procured by a substance bond, for example by welding. In FIG. 3, tool 16 has been omitted.

Movable tool 14 and immovable tool 16 are configured as punching tools and comprise for this purpose sharpened regions 60a, 60b and/or 62a, 62b configured as cutting teeth. Sharpened regions 60a, 60a and 62a, 62b, respectively, coact to cuttingly dissect tissue when movable tool 14 is pushed and/or pressed from its position shown in FIGS. 1 and 2 in distal direction against immovable tool 16.

In the region of tools 14 and 16, bar 48 further comprises lateral grooves 64 and 66, which are engaged by webs 68 and 70 fixed to sleeve section 58 of movable tool 14. The system comprising grooves 64 and 66 and webs 68 and 70 produces a protection from torsion for movable tool 14 relative to bar 48, so that immovable tool 16 and movable tool 14 are always retained in unchanged position one relative to the other, in pivotal direction about the longitudinal axis of shaft 12.

Referring once more to FIG. 1, tube 38 and bar 48 jointly extend to handle 18 at the proximal end of shaft 12.

In this arrangement, bar 48 extends to a holder 72 that is firmly and immovably connected with immovable grip element 22.

In FIG. 7, immovable grip element 22 is illustrated in isolation. A bore 74 is provided in holder 72, in which the extreme proximal end of bar 48 is received and firmly anchored, for example by means of a screw (not shown) screwed laterally into holder 72 (see also FIG. 10).

Immovable grip element 22 comprises further a stationary tube end 76 through which tube 38 and bar 48 are guided. While bar 48 is immovable relative to tube end 76, tube 38 can be displaced axially relative to tube end 76.

Tube 38 in its turn is connected in non-positive fashion with a rider 78 fixed to movable grip element 20. In FIGS. 8 and 9 rider 78 is illustrated in isolation. While the extreme proximal end of tube 38 is fixed to rider 78 in a distal region 80 of a bore 82, bar 48 is guided through bore 82 to holder 72. Consequently, rider 78 can be axially moved relative to bar 48.

As appears from FIG. 1, tube end 76 is further followed, distally, by a tube end 84, fixed to immovable grip element 22, in which a guide tube 86 is mounted, being therefore immovable. Tube 38 of force transmission element 34 and bar 48 of shaft 12 extend through guide tube 86.

Further arranged in tube end 84 is a connection 88 for connecting a rinsing line, so that the rinsing liquid can be introduced through tube 38 and bar 48 and can be guided to the distal end of shaft 12, as has been described before.

Further, bar 48 can be removed from tube 38 in the case of instrument 10, which is rendered possible, in spite of bend 63, through helical spring 40 in the region of bend 36. In order to permit bar 48 to be withdrawn from force transmission element 34 in the form of tube 38 and helical spring 40, and movable tool 14 connected with the latter, movable tool 14, especially its sleeve section 58, exhibit a short overall length, in axial direction, so that bar 48, with its bend 36, can be withdrawn through movable tool 14. In addition, grooves 50, 64 and 66 then extend over the whole length of bar 48, contrary to the representation of FIGS. 2 and 3.

The function of instrument 10 will now be described in more detail.

Starting out from the operating position illustrated in FIG. 1, in which movable tool 14 occupies its extreme proximal position, rider 78 and, consequently, tube 38 fixed thereto are axially displaced in distal direction by moving movable grip element 20 toward immovable grip element 22, while bar 48 remains stationary. The axial movement is transferred from tube 38 via helical spring 40 over bend 36 of shaft 12 to movable tool 14, whereby the latter is displaced toward the immovable tool 16. Consequently, force transmission element 34 exerts thrust when dissecting tissue. Due to the closely wound windings of helical spring 40, the latter is not compressed by the thrust exerted by tube 38, the force being directly transmitted to movable tool 14. By moving movable grip element 20 back to its position illustrated in FIG. 1, flexible pull element 52 illustrated in FIG. 2 now has the effect that movable tool 14 is safely withdrawn when force transmission element 34 exerts tension, flexible pull element 52 preventing any axial extension of helical spring 40 during withdrawal of tube 38.

Figure 11:
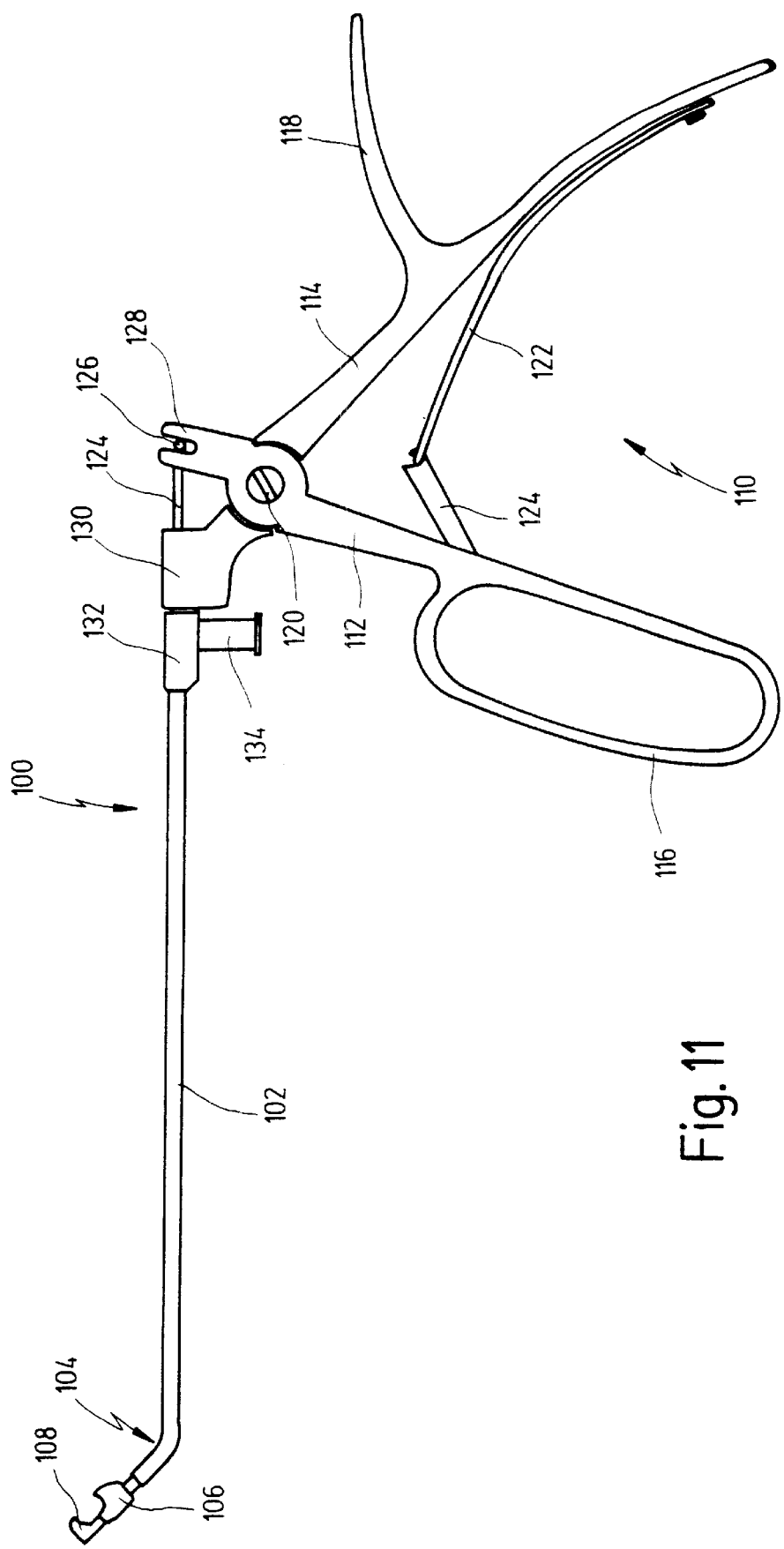
FIG. 11 shows an overall side view of one embodiment of a medical instrument according to the second aspect.

The illustration of FIG. 11 shows a medical instrument, indicated generally by reference numeral 100, for dissecting tissue in the human or animal body, as a first embodiment of the second aspect of to the invention.

The instrument 100 comprises an elongated shaft 102. Shaft 102 is configured as a tubular shaft. Shaft 102 comprises a bend 104 arranged in the region of the distal end of shaft 102. Bend 104 defines a plane of curvature being at the same time the plane of drawing of FIG. 11.

A movable tool 106 is arranged at the distal end of the shaft 102. Arranged at the extreme distal end of shaft 102 is an immovable tool 108, movable tool 106 being axially displaceable relative to immovable tool 108 in order to coact with immovable tool 108 in the manner of a punch for the purpose of dissecting tissue.

A handle 110, similar to handle 18 in FIG. 1, is arranged at the proximal end of shaft 102. Handle 110 comprises a movable grip element 112 and an immovable grip element 114.

Movable grip element 112 comprises a ring 116, through which one, two or three fingers of one hand can be slipped for actuating movable grip element 112. Immovable grip element 114 is provided with an extension 118, projecting in proximal direction, against which the hollow between thumb and index finger comes to rest when the hand grasps handle 110.

Movable grip element 112 and immovable grip element 114 are pivotally connected one to the other via a hinged joint 120.

Fixed to immovable grip element 114 is a leaf spring 122, which is connected with a lever 124 pivoted on movable grip element 112. Together with lever 124, leaf spring 122 biases movable grip element 112 to its open position shown in FIG. 11, in which it is spaced from immovable grip element 114.

Movable tool 106 is connected in non-positive fashion with movable grip element 112 by a force transmission element 124 extending along shaft 102 inside the latter. Force transmission element 124 is axially movable relative to shaft 102.

An extreme proximal end of force transmission element 124 comprises a pin 126, that extends transversely to the lengthwise direction of force transmission element 124 and is fitted in a fork section 128 of movable grip element 112.

Force transmission element 124 is guided in a tube end 130 fixed to immovable grip element 114 in movable fashion relative to tube end 130, to which shaft 112 is immovably fixed via a further tube end 132. Further mounted on tube end 132 is a connection 134 for connecting a rinsing line—not shown—for introducing rinsing liquid into shaft 102, which is then led inside shaft 102 to the distal end thereof, where it is discharged from shaft 102 into the operating region.

Figure 12:
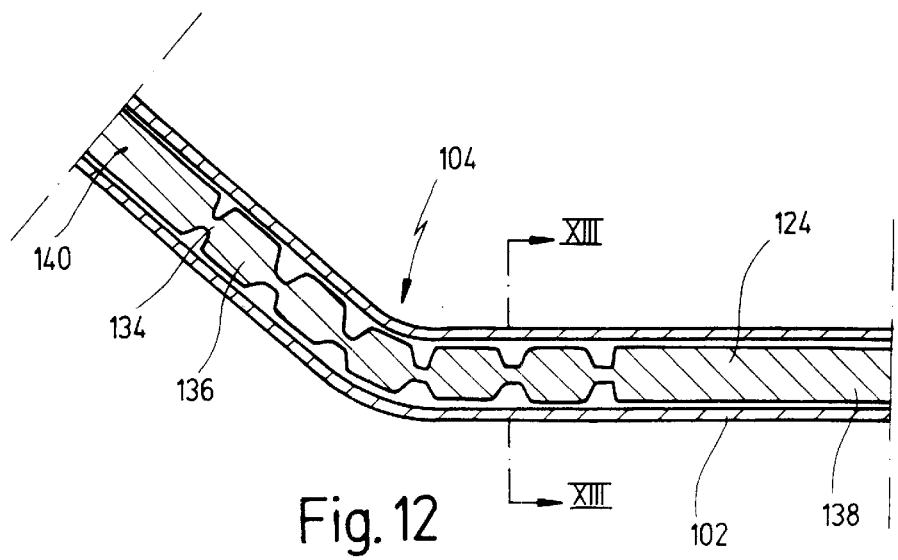
FIG. 12 shows a detail of the instrument according to FIG. 11, partly as longitudinal section, in the region of the bend of the shaft, representing schematically a first embodiment of a force transmission element.
Figure 13:
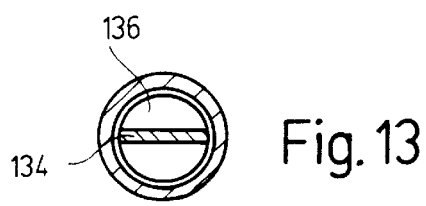
FIG. 13 shows a section taken along line XIII—XIII in FIG. 12.

According to FIGS. 12 and 13, force transmission element 124 is locally flattened in the region of bend 104, namely at a plurality of flattened sections 124 of which force transmission element 124 comprises a total of six in the embodiment illustrated in FIG. 12.

In sections 134, force transmission element 124 is flattened transversely to the plane of curvature so that force transmission element 124 is flexible in the plane of curvature of bend 104 and can adapt itself to curved shape of shaft 102 in the region of bend 104.

In intermediate sections 136, which consist of solid material, force transmission element 124 is in contact with shaft 102 by its circumference.

Intermediate sections 136 are configured as cylindrical bodies, the circumferential sides of intermediate sections 136 being in contact with shaft 102, being slightly convex in longitudinal direction so that each of intermediate sections 136 is in contact with shaft 102 only along a line, whereby friction between intermediate sections 136 and shaft 102 is minimized.

While force transmission element 124 extends over the width of shaft 102 in the region of intermediate sections 136, transversely to the plane of curvature, i.e. transversely to the plane of drawing of FIG. 12, this is true also for flattened sections 134 in which force transmission element 124 likewise extends over the inner diameter of shaft 102, as can be seen best in FIG. 13. Flattened sections 134 therefore form section s in which force transmission element 124 is locally configured as a flat band.

The axial length of flattened sections 134 is small compared with the axial length of intermediate sections 136. Sections 134 can be reduced to short incisions, which exhibit roughly the shape of a V in the longitudinal section of force transmission element 124. However, it is also possible to select different relationships between the lengths of sections 134 and 136.

Due to the special configuration of force transmission element 124 the latter is flexible only in the direction of curvature of shaft 102, while being not flexible, but rather rigid, in transverse direction to the plane of curvature of bend 104.

In the region outside bend 104, force transmission element 124 is configured as a bar 138 that exhibits a circular cross-section and which is guided inside shaft 102, in contact with the latter.

A distal section 140 of force transmission element 124 is suitably connected with movable tool 106 in non-positive relationship, in order to move latter relative to immovable tool 108 when movable grip element 112 is actuated.

Flattened sections 134 of force transmission element 124 are formed by flattening force transmission element 124, which originally has the shape of a bare, from two circumferentially opposite sides of the force transmission element 124 by means of a machining operation, for example by milling, in such a way that the flats are produced in equal positions, axially.

Figure 12A:
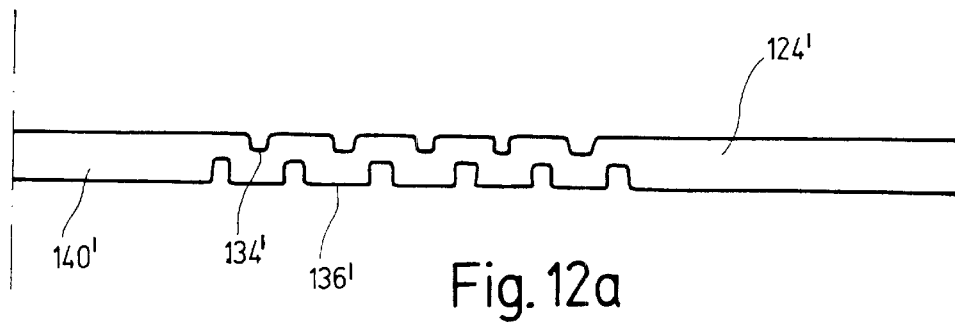
FIG. 12a) shows an embodiment, modified by comparison with FIG. 12, of an isolated force transmission element.

In contrast, FIG. 12a) shows a force transmission element 124' where flattened sections 134' are formed on two circumferentially opposite sides of force transmission element 124', but are axially offset in the way of a meander. Correspondingly, intermediate sections 136' are likewise axially offset one relative to the other. With this configuration, force transmission element 124' also extends in the flattened sections 134' over the full inner diameter of the shaft—not shown in the drawing.

Figure 14:
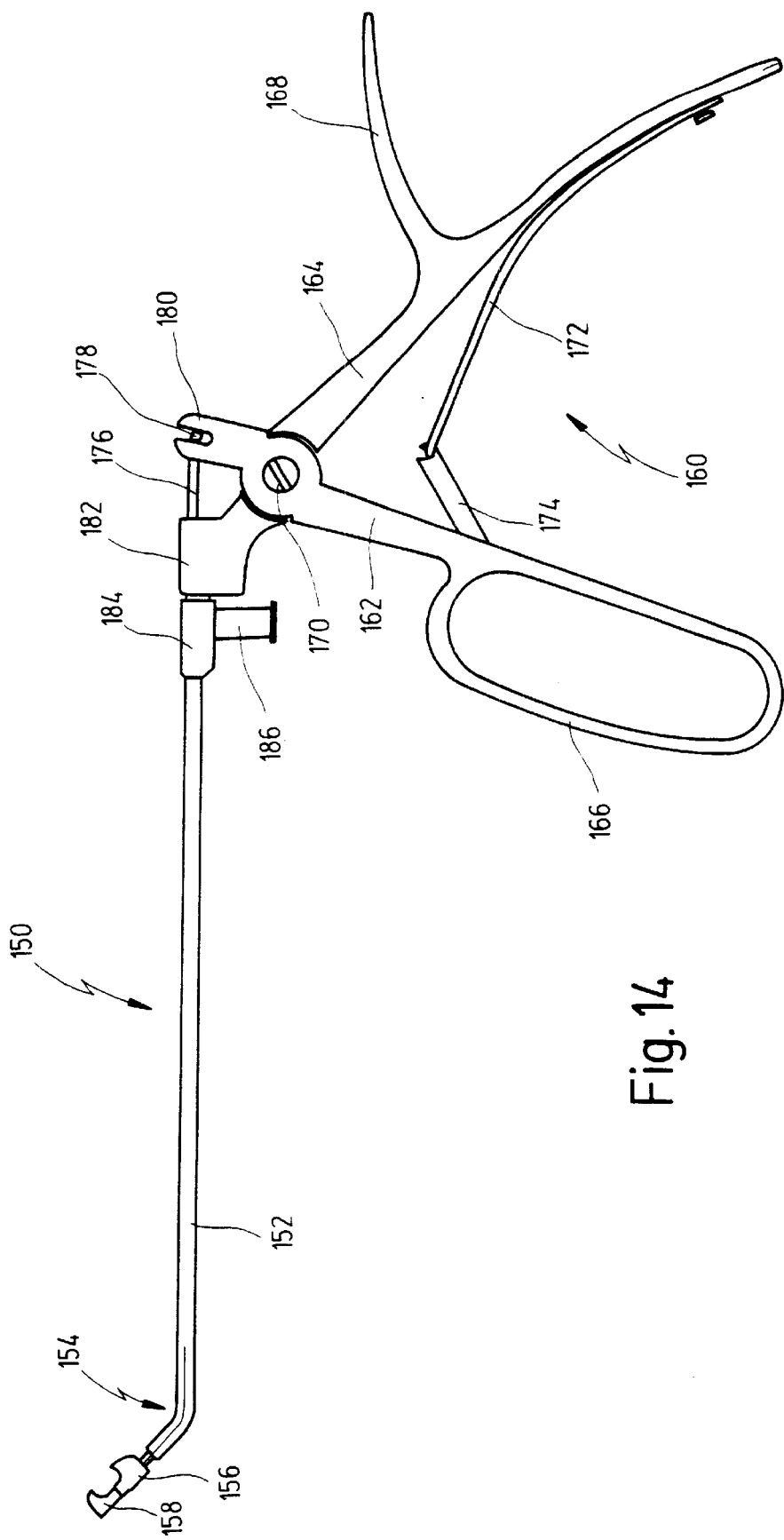
FIG. 14 shows an overall side view of an embodiment of the third aspect of a medical instrument according to the invention.
Figure 15:
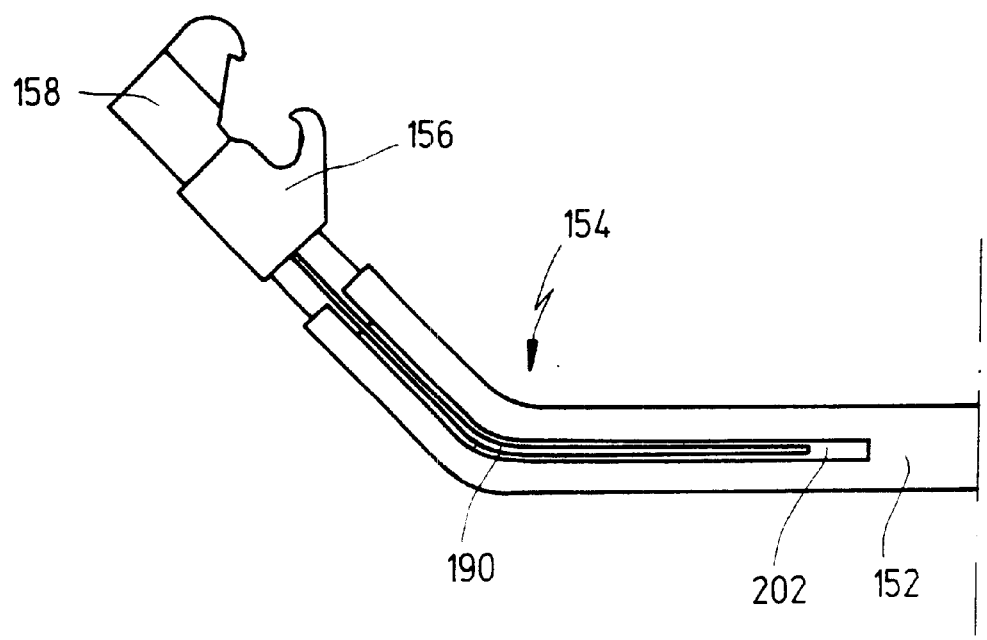
FIG. 15 shows a side view, in enlarged scale, of the distal end of the instrument according to FIG. 14.

FIG. 14 shows an embodiment of a medical instrument according to the third aspect of the invention, indicated generally be reference numeral 150, for dissecting tissue in the human or animal body, which is modified with respect to the force transmission element, compared with the previously described embodiment, as will be described hereafter in more detail.

Instrument 150 comprises an elongated shaft 152 which comprises a bend 154.

A movable tool 156 is arranged at the distal end of shaft 152, tool 156 being axially movable and coacting, in the way of a punch, with an immovable tool 158 likewise arranged at the distal end of shaft 152.

A handle 160 comprising a movable grip element 162 and an immovable grip element 164 is arranged at the proximal end of shaft 152.

Movable grip element 162 comprises a ring 166, through which one, two or three fingers of one hand can be slipped for actuating movable grip element 162.

Immovable grip element 164 is provided with an extension 168, projecting in proximal direction, against which the hollow between thumb and index finger comes to rest when the hand grasps handle 160.

Movable grip element 162 and immovable grip element 164 are pivotally connected one to the other via a hinged joint 170.

Fixed to immovable grip element 164 is a leaf spring 172, which is connected with a lever 174 pivoted on movable grip element 162. Together with lever 174, leaf spring 172 biases movable grip element 162 to its open position shown in FIG. 14, in which it is maximally spaced from immovable grip element 164.

Movable tool 156 is operatively connected in non-positive fashion with the movable grip element 162 by a force transmission element 176 extending through shaft 152.

At an extreme proximal end of force transmission element 176 there is provided a pin 178, extending transversely to the lengthwise direction of force transmission element 176, which engages a fork section 180 of movable grip element 162, whereby force transmission element 176 is connected, in non-positive fashion, with moveable grip element 162.

Force transmission element 176 is guided through a tube end 182, fixed to immovable grip element 164, on which shaft 152 is fixed via another tube end 184.

Mounted on tube end 184 is a connection 186 for connecting a rinsing line—not shown—for introducing rinsing liquid through the connection 186 into shaft 152, which is then led through shaft 152 to the distal end thereof, where it is discharged into the operating region.

Figure 16:
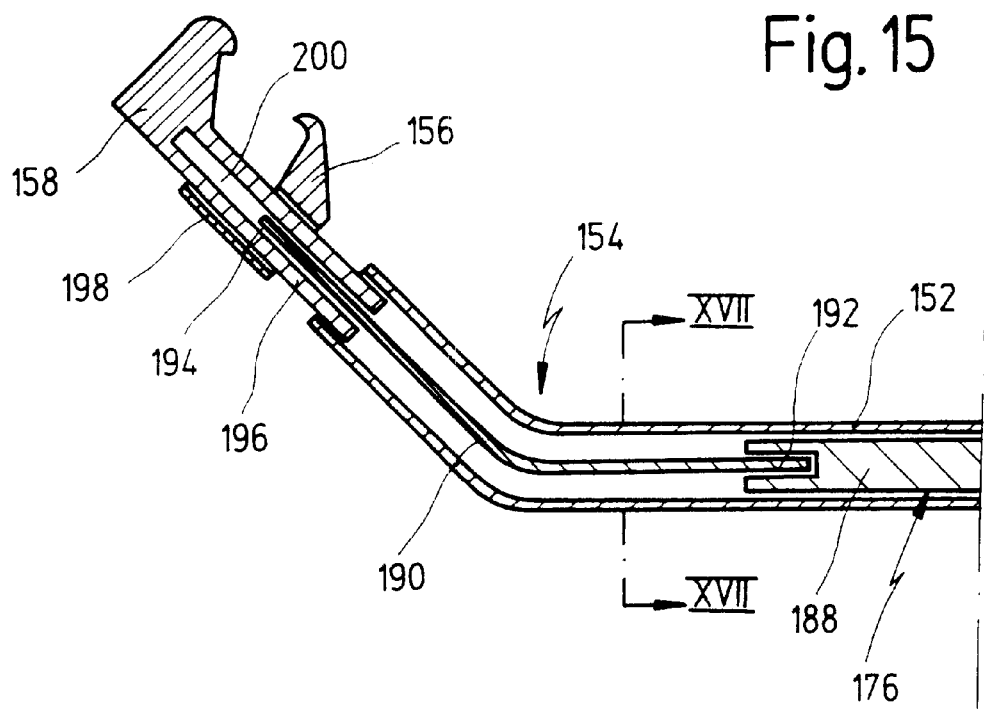
FIG. 16 shows a longitudinal section corresponding to FIG. 15.
Figure 17:
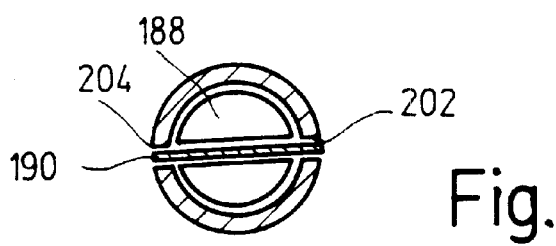
FIG. 17 shows a section taken along line XVII—XVII in FIG. 16.

According to FIG. 16, force transmission element 176 is configured as a bar 188 between movable grip element 162 and bend 154. Bar 188 exhibits a circular cross-section; it is in contact with shaft 152 and is guided by the latter during its axial reciprocating movements.

In the region of bend 154, force transmission element 176 is configured as a flexible continuous flat band 190. Flat band 190 may be configured, for example, as a leaf spring made from spring steel.

The flat band is oriented in such a way that the surface normal of its broad flat sides lies in the plane of curvature of bend 154, which means that the flat broad sides of band 190 extend transversely to the plane of curvature. By giving flat band 190 this configuration, force transmission element 176 is flexible in the region of bend 154, in the plane of curvature of bend 154, so that it can always adapt itself to the form of bend 154.

A proximal end 192 of band 190 is connected by a substance bond with bar 188 of force transmission element 176, for example by laser welding. It may, however, also be provided to produce flat band 190 from solid bar 188 by a material removing machining operation so that flat band 190 and bar 188 are made as a single unit.

A distal end 194 of flat band 190 is connected by a substance bond with movable tool 156, whereby the non-positive connection of force transmission element 176 with movable tool 156 is achieved.

Movable tool 156 is mounted, in axially displaceable fashion, on immovable tool 158 which is provided for this purpose with a tubular extension 196 on which a sleeve section 198 of movable tool 156 is slidingly seated.

Tubular extension 196 of immovable tool 158 in its turn is fixed to the distal end of shaft 152, for example by welding. Further, a continuous lateral slot 200 is provided in tubular extension 196, in which flat band 190 is received in axially sliding relationship.

In the region of bend 154, shaft 152 comprises two guides 202 and 204 provided in the wall of shaft 152 in the form of slots extending through the wall of shaft 152 so that shaft 152 is open in the region of guides 202 and 204.

Transversely to the longitudinal direction of shaft 152, flat band 190 extends not only over the inner diameter, but also over the entire outer diameter of shaft 152, so that its narrow sides engage guides 202 and 204, whereby flat band 190 is guided in guides 202 and 204 along bend 154 of shaft 152.

What we claim is:

1. A medical instrument for dissecting tissue in the human or animal body, comprising:
    a shaft having a distal end and a proximal end, said shaft having at least one bend between said distal and said proximal end;
    at least one movable tool disposed at said distal end of said shaft;
    at least one movable grip element disposed at said proximal end of said shaft;
    a reciprocal force transmission element for transmitting thrust and pull forces, and having a distal end and a proximal end and extending along said shaft and, further, being axially movable relative to said shaft, said proximal end of said reciprocal force transmission element being operatively interconnected to said at least one movable grip element and said distal end of said reciprocal force transmission element being operatively interconnected to said at least one movable tool for transmitting a force from said at least one movable grip to said at least one movable tool;
    said reciprocal force transmission element being configured, in an area proximate to said at least one bend, flattened transverse to a plane of curvature of said at least one bend and said reciprocal force transmission element extending in the region of said at least one bend in a direction transverse to said plane of curvature of said at least one bend continuously in axial direction at least over an inner diameter of said shaft, and said reciprocal force transmission element comprising a plurality of axially spaced flattened sections,
    wherein said reciprocal force transmission element is in contact by its circumference with said shaft in intermediate sections between said flattened sections, and wherein said intermediate sections extend to both a concave and a convex inner side of said bend of said shaft.

2. The instrument of claim 1, wherein said flattened sections of said reciprocal force transmission element are formed from solid material by a machining process, said material being removed from two opposite circumferential sides of said reciprocal force transmission element transversely to a longitudinal direction of said reciprocal force transmission element.

3. The instrument of claim 1, wherein each of said flattened sections is formed at the same axial position from two opposite sides of the circumference of said reciprocal force transmission element.

4. The instrument of claim 1, wherein said flattened sections are formed in axially offset arrangement from opposite sides of the circumference of said reciprocal force transmission element.

5. The instrument of claim 1, wherein said reciprocal force transmission element is configured as a solid bar, consisting of solid material, in regions outside said bend.

6. The instrument of claim 1, wherein said at least one movable tool is axially movable relative to said shaft, and a second tool is arranged at said distal end of said shaft, said movable tool and said second tool acting together in the way of a punch if moved axially one relative to the other.

7. The instrument of claim 6, wherein said second tool is connected with said shaft immovably, and is arranged distally before said movable tool.

8. The instrument of claim 7, wherein said movable tool is protected from torsion relative to said second tool.

9. The instrument of claim 1, wherein said at least one movable tool is configured as a jaw part which can be pivoted about a hinge joint and which coacts with a second tool in the manner of a pair of scissors or a forceps.

* * * * *